US00PP25367P2

(12) United States Plant Patent
Kanazawa

(10) Patent No.: US PP25,367 P2
(45) Date of Patent: Mar. 24, 2015

(54) ***ANEMONE* PLANT NAMED 'CINDERELLA'**

(50) Latin Name: *Anemone hupehensis*
Varietal Denomination: Cinderella

(71) Applicant: Yoshihiro Kanazawa, Yamaturi-Machi (JP)

(72) Inventor: Yoshihiro Kanazawa, Yamaturi-Machi (JP)

(73) Assignee: Osco Garden B.V., Aalsmeer (NL)

( * ) Notice: Subject to any disclaimer, the term of this patent is extended or adjusted under 35 U.S.C. 154(b) by 139 days.

(21) Appl. No.: 13/815,653

(22) Filed: Mar. 13, 2013

(51) Int. Cl.
*A01H 5/00* (2006.01)

(52) U.S. Cl.
USPC ..... Plt./263.1

(58) Field of Classification Search
CPC ..... A01H 5/02; A01H 5/025
USPC ..... Plt./263.1
See application file for complete search history.

*Primary Examiner* — June Hwu
(74) *Attorney, Agent, or Firm* — C. A. Whealy

(57) ABSTRACT

A new and distinct cultivar of *Anemone* plant named 'Cinderella', characterized by its upright and compact plant habit; moderately vigorous growth habit; freely flowering habit; single-type flowers that are light purple in color; and good garden performance.

2 Drawing Sheets

Botanical designation: *Anemone hupehensis.*
Cultivar denomination: 'CINDERELLA'.

BACKGROUND OF THE INVENTION

The present invention relates to a new and distinct cultivar of *Anemone*, botanically known as *Anemone hupehensis* and hereinafter referred to by the name 'Cinderella'.

The new *Anemone* plant is a product of a planned breeding program conducted by the Inventor in Yamatsuri-machi, Fukushima-ken, Japan. The objective of the breeding program is to create new compact *Anemone* plants with numerous attractive flowers.

The new *Anemone* plant originated from a cross-pollination made by the Inventor in October, 1995 in Yamatsuri-machi, Fukushima-ken, Japan of an unnamed proprietary selection of *Anemone hupehensis*, not patented, as the female, or seed, parent, with *Anemone hupehensis* 'Diana', not patented, as the male, or pollen, parent. The new *Anemone* plant was discovered and selected by the Inventor as a single flowering plant within the progeny of the stated cross-pollination in a controlled greenhouse environment in Yamatsuri-machi, Fukushima-ken, Japan in October, 1997.

Asexual reproduction of the new *Anemone* by root cuttings in a controlled environment in Yamatsuri-machi, Fukushima-ken, Japan since October, 1997 has shown that the unique features of this new *Anemone* plant are stable and reproduced true to type in successive generations.

SUMMARY OF THE INVENTION

Plants of the new *Anemone* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'Cinderella'. These characteristics in combination distinguish 'Cinderella' as a new and distinct *Anemone* plant:

1. Upright and compact plant habit.
2. Moderately vigorous growth habit.
3. Freely flowering habit.
4. Single-type flowers that are light purple in color.
5. Good garden performance.

Plants of the new *Anemone* can be compared to plants of the female parent selection. Plants of the new *Anemone* differ primarily from plants of the female parent selection in the following characteristics:

1. Plants of the new *Anemone* have stronger roots than plants of the female parent selection.
2. Plants of the new *Anemone* are more freely flowering than plants of the female parent selection have single type flowers.

Plants of the new *Anemone* can be compared to plants of the male parent, 'Diana'. Plants of the new *Anemone* differ primarily from plants of 'Diana' in the following characteristics:

1. Plants of the new *Anemone* are more compact than plants of 'Diana'.
2. Plants of the new *Anemone* and 'Diana' differ in flower color as plants of 'Diana' have pink-colored flowers.

Plants of the new *Anemone* can be compared to plants of *Anemone hupehensis* 'Pretty Lady Susan', disclosed in U.S. Plant Pat. No. 22,331. In side-by-side comparisons conducted in Mijdrecht, The Netherlands, plants of the new *Anemone* and 'Pretty Lady Susan' differed primarily in the following characteristics:

1. Plants of the new *Anemone* were more compact than plants of 'Pretty Lady Susan'.
2. Plants of the new *Anemone* flowered later than plants of 'Pretty Lady Susan'.
3. Plants of the new *Anemone* and 'Pretty Lady Susan' differed in flower color as plants of 'Pretty Lady Susan' had deep pink-colored flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'Cinderella' in a container.

The photograph on the second sheet comprises a close-up view of a typical flower of 'Cinderella'.

DETAILED BOTANICAL DESCRIPTION

The aforementioned photographs and following observations, measurements and values describe plants grown in 17-cm containers during the summer in an outdoor nursery in Mijdrecht, The Netherlands and under cultural practices typical of commercial *Anemone* production. During the production of the plants, day temperatures ranged from 14° C. to 28° C. and night temperatures ranged from 6° C. to 16° C. Plants were four months old when the photographs and description were taken. In the following description, color references are made to The Royal Horticultural Society Colour Chart, 2007 Edition, except where general terms of ordinary dictionary significance are used.

Botanical classification: *Anemone hupehensis* 'Cinderella'.

Parentage:

*Female, or seed, parent*.—Unnamed proprietary selection of *Anemone hupehensis*, not patented.

*Male, or pollen, parent*.—*Anemone hupehensis* 'Diana', not patented.

Propagation:

*Type*.—In vitro propagation.

*Time to initiate roots, summer*.—About 15 days at temperatures of 20° C. to 25° C.

*Time to initiate roots, winter*.—About 25 days at temperatures of 15° C. to 20° C.

*Root description*.—Medium in thickness, fleshy; white in color.

*Rooting habit*.—Moderately freely branching; medium density.

Plant description:

*Plant and growth habit*.—Herbaceous perennial; upright and compact plant habit with leaves developing from basal rosettes; about 13 basal rosettes developing per plant; moderately vigorous growth habit.

*Plant height*.—About 45.8 cm.

*Plant diameter*.—About 41.3 cm.

Foliage description:

*Arrangement*.—Alternate, compound with three leaflets per leaf.

*Length, leaves*.—About 9.6 cm.

*Width, leaves*.—About 7.1 cm.

*Length, leaflets*.—About 7 cm.

*Width, leaflets*.—About 3.9 cm.

*Shape, leaves*.—Broadly ovate.

*Shape, leaflets*.—Ovate to broadly ovate.

*Apex, leaflets*.—Acute.

*Base, leaflets*.—Obtuse to hastate.

*Margin, leaflets*.—Bi-serrate.

*Texture, leaflets, upper surface*.—Smooth, glabrous.

*Texture, leaflets, lower surface*.—Sparsely pubescent along veins.

*Venation pattern, leaflets*.—Palmate, laciniate.

*Color*.—Developing leaflets, upper surface: Close to between 143A and 144A. Developing leaflets, lower surface: Close to 148A to 148B. Fully expanded leaflets, upper surface: Close to between N137A and 147A; venation, close to 144B. Fully expanded leaflets, lower surface: Close to 147B; venation, close to 146B to 146C.

*Leaf petiole*.—Length: About 13.1 cm. Diameter: About 2 mm. Texture, upper and lower surfaces: Smooth, glabrous. Color, upper and lower surfaces: Close to 144A.

Flower description:

*Flower arrangement and flowering habit*.—Single-type rose-like flowers arranged in simple and compound cymes; freely flowering habit with seven flowers develop per inflorescence and about 80 flowers developing per plant; flowers face mostly upright to slightly outwardly.

*Fragrance*.—None detected.

*Natural flowering season*.—Plants of the new *Anemone* begin flowering about 10.5 months after planting and flower during the late summer in The Netherlands.

*Flower longevity*.—Individual flowers last about one week on the plant; flowers not persistent.

*Inflorescence height*.—About 15.9 cm.

*Inflorescence diameter*.—About 14.4 cm.

*Flower diameter*.—About 5.1 cm.

*Flower length (depth)*.—About 1.3 cm.

*Flower buds*.—Length: About 9 mm. Diameter: About 9.5 mm. Shape: Globular. Color: Close to 187B; stripes, close to N155A; base strongly tinged with close to 145A and 149B.

*Petals*.—Absent.

*Sepals*.—Quantity and arrangement: Five arranged in a single whorl. Length: About 2.5 cm. Width: About 2.1 cm. Shape: Broadly obovate to broadly elliptic. Apex: Obtuse or emarginate. Base: Acute. Margin: Entire. Texture, upper surface: Glabrous, smooth, velvety. Texture, lower surface: Densely pubescent. Color: When opening, upper surface: Close to 76D flushed slightly with close to 146D; towards the margins, close to 7B. When opening, lower surface: Close to 187B to 187C; towards the margins, close to 60C. Fully opened, upper surface: Close to between 75B, 76B and 77C; towards the base, close to 69D flushed with close to 145D; color does not fade with development. Fully opened, lower surface: Close to between 187D, 70A and 76A.

*Peduncles*.—Length: About 25.4 cm. Diameter: About 3 mm. Aspect: Mostly erect to 30° from vertical. Strength: Moderately strong. Color: Close to 144A; towards the apex, slightly tinged with close to N187A.

*Pedicels*.—Length: About 7.8 cm. Diameter: About 1.5 mm. Aspect: Erect to about 35° from the peduncle axis. Strength: Strong. Color: Close to 138A tinged with close to 201B.

*Reproductive organs*.—Androecium: Stamen number per flower: About 200. Filament length: About 7 mm. Filament color: Close to 157D. Anther shape: Reniform. Anther length: About 1.5 mm. Anther color: Close to 15B. Amount of pollen: Scarce. Pollen color: Close to 8C. Gynoecium: Pistil number per flower: About 200. Pistil length: About 1 mm. Stigma shape: Club-shaped. Stigma color: Close to 144B. Style length: About 0.5 mm. Style color: Close to 145A. Ovary color: Close to 145A.

*Seeds and fruits*.—Seed and fruit development have not been observed on plants of the new *Anemone*.

Garden performance: Plants of the new *Anemone* have been observed to have good garden performance, to tolerate high temperatures of about 35° C. and to be hardy to USDA Hardiness Zone 4.

Pathogen & pest resistance: Plants of the new *Anemone* have not been observed to be resistant to pests and pathogens common to *Anemone* plants.

It is claimed:

1. A new and distinct *Anemone* plant named 'Cinderella' as illustrated and described.

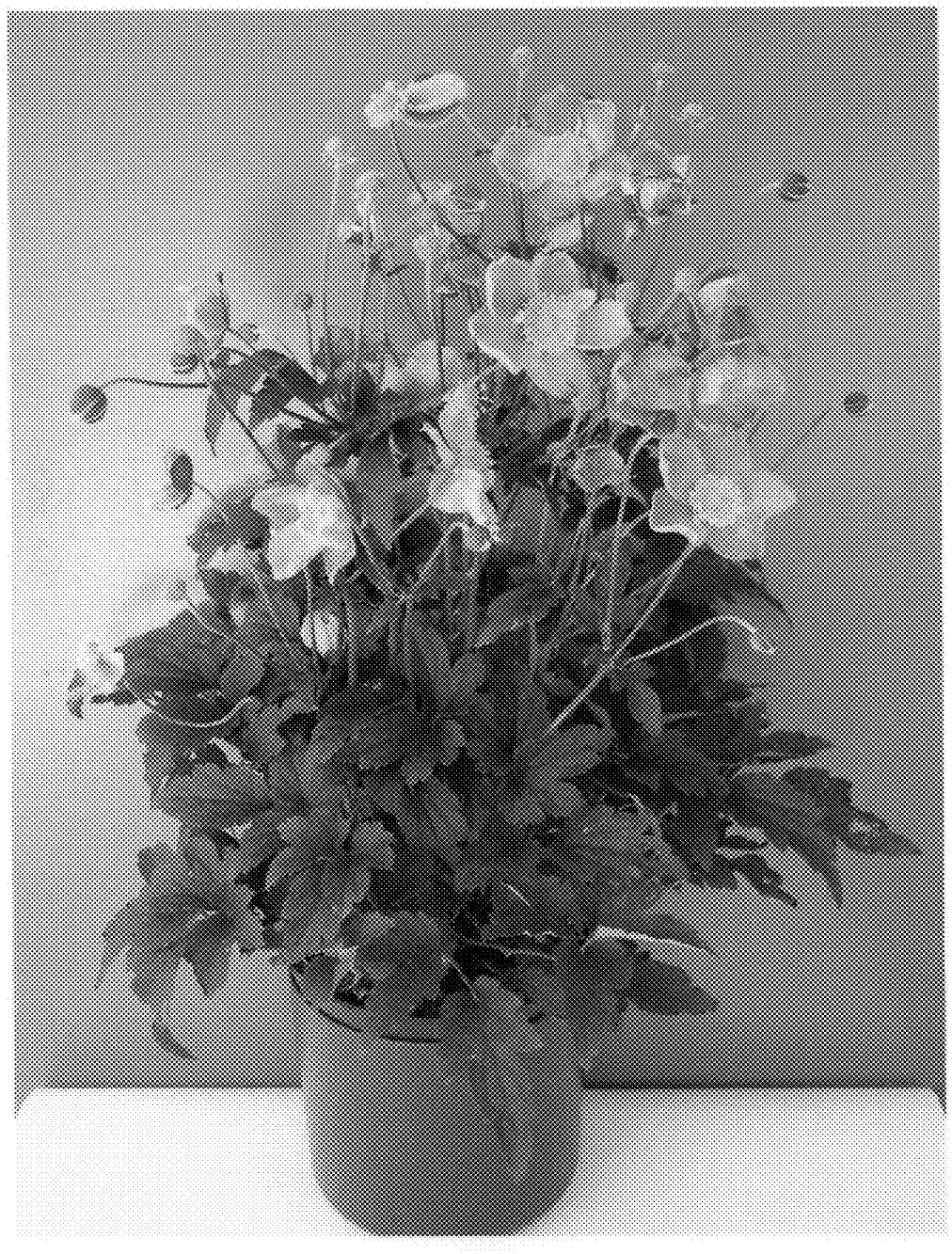

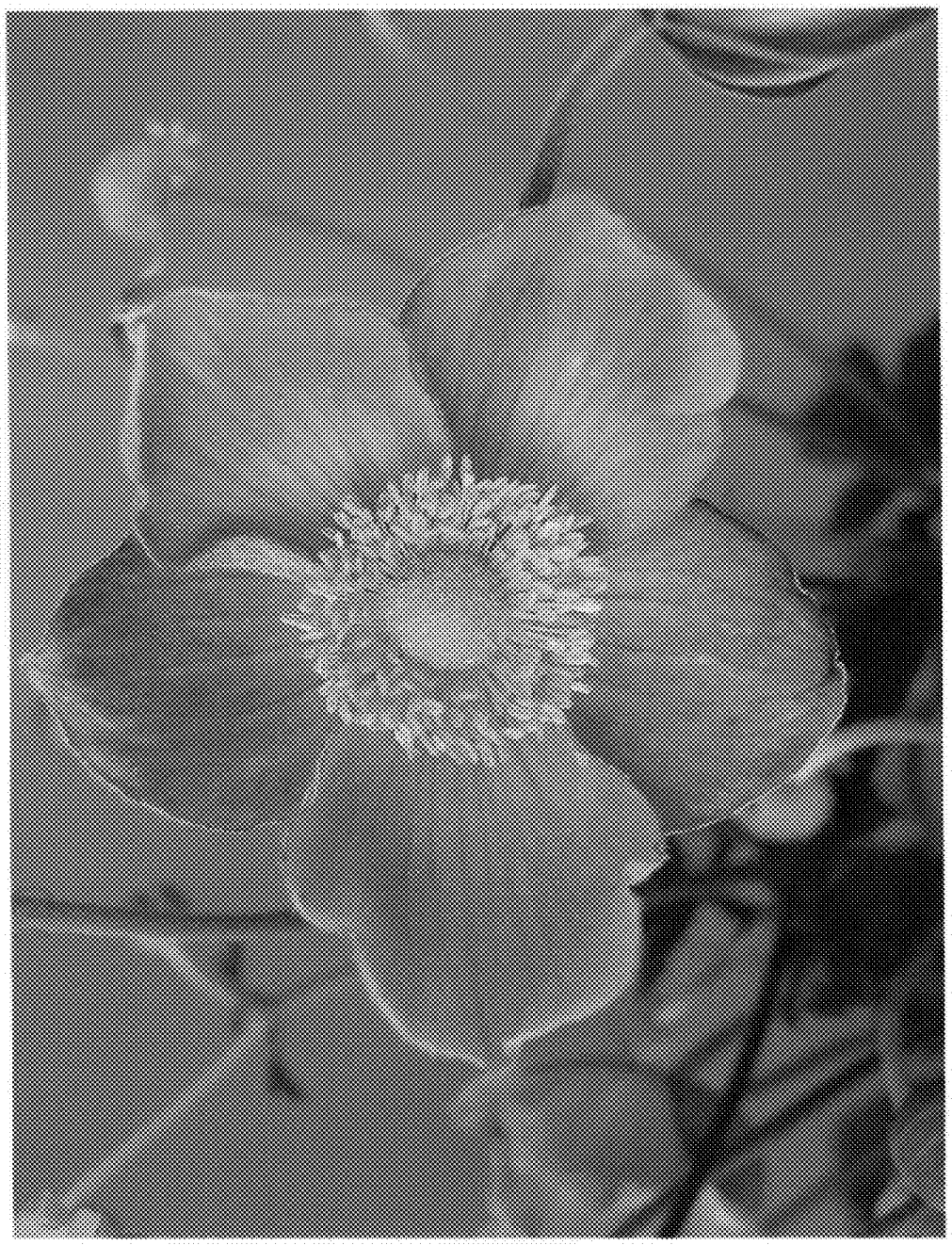

* * * * *